US012721829B2

(12) United States Patent
Tarkowski

(10) Patent No.: US 12,721,829 B2
(45) Date of Patent: Sep. 1, 2026

(54) **PERMETHRIN FOR USE IN THE TREATMENT OF *DEMODEX* SPECIES INFESTATION**

(71) Applicant: TG PHARMA SPOLKA Z OGRANICZONA ODPOWIEDZIALNOSCIA, Warsaw (PL)

(72) Inventor: Witold Tarkowski, Tarnow (PL)

(73) Assignee: TG PHARMA SPOLKA Z OGRANICZONA ODPOWIEDZIALNOSCIA, Warsaw (PL)

(*) Notice: Subject to any disclaimer, the term of this patent is extended or adjusted under 35 U.S.C. 154(b) by 472 days.

(21) Appl. No.: 18/248,949

(22) PCT Filed: Oct. 15, 2021

(86) PCT No.: PCT/IB2021/059492
§ 371 (c)(1),
(2) Date: Apr. 13, 2023

(87) PCT Pub. No.: WO2022/079675
PCT Pub. Date: Apr. 21, 2022

(65) Prior Publication Data

US 2023/0381129 A1 Nov. 30, 2023

(30) Foreign Application Priority Data

Oct. 16, 2020 (PL) ........................................ 435706

(51) Int. Cl.

| | |
|---|---|
| ***A61K 31/216*** | (2006.01) |
| ***A61K 9/00*** | (2006.01) |
| ***A61K 31/42*** | (2006.01) |
| ***A61P 33/14*** | (2006.01) |

(52) U.S. Cl.
CPC .......... *A61K 31/216* (2013.01); *A61K 9/0014* (2013.01); *A61K 31/42* (2013.01); *A61P 33/14* (2018.01)

(58) Field of Classification Search
None
See application file for complete search history.

(56) References Cited

U.S. PATENT DOCUMENTS

| | | | |
|---|---|---|---|
| 2004/0161441 | A1 | 8/2004 | Sirinyan et al. |
| 2018/0020667 | A1 | 1/2018 | Barros |
| 2019/0307128 | A1 | 10/2019 | Pinto et al. |
| 2020/0031859 | A1 | 1/2020 | Santos et al. |

FOREIGN PATENT DOCUMENTS

| | | | |
|---|---|---|---|
| CL | 2016002178 | A1 | 11/2017 |
| CL | 2018001681 | A1 | 10/2018 |
| EP | 2279736 | A1 | 2/2011 |
| EP | 2310000 | A1 | 4/2011 |
| EP | 2791354 | A1 | 10/2014 |
| JP | 2004525188 | A | 8/2004 |
| WO | 19113475 | A1 | 6/2019 |
| WO | 20023943 | A1 | 1/2020 |
| WO | 2020201440 | A1 | 10/2020 |

OTHER PUBLICATIONS

Fortsinger. Journal of the American Academy of Dermatology, 1999, 41(5), 775-777 (Year: 1999).*
Slawson. American Family Physician, 2003, 67(8), 1782-1784 (Year: 2003).*
Raoufinejad. Journal of the European Academy of Dermatology and Venerology, 2016, 30, 2106-2117 (Year: 2016).*
Dominey A et al: "Pityriasis folliculorum revisited", Journal of the American Academy of Dermatology, Mosby, Inc, US, vol. 21, No. 1, Jul. 1, 1989, pp. 81-84.
Diona Damian et al: "Demodex infestation in a child with leukaemia: treatment with ivermectin and permethrin", International Journal of Dermatology, Wiley-Blackwell Publishing Ltd, UK, vol. 42, No. 9, Sep. 3, 2003, pp. 724-726.
Koyak M, Yagli S, Vahapoglu G, Eklioglu M., Permethrin 5% cream versus metronidazole 0.75% gel for the treatment of papulopustular rosacea. A randomized double-blind placebo-controlled study. Dermatology, 2002, vol. 205, No. 3, pp. 265-270.
Hecht, Idan et al., Permethrin Cream for the Treatment of Demodex Blepharitis. Dec. 2019, vol. 38/12, pp. 1513-1518.
Zewe, Christine M., et al. "Afoxolaner and fluralaner treatment do not impact on cutaneous Demodex populations of healthy dogs." Veterinary Dermatology vol. 28.5 (2017): pp. 468-e107.

* cited by examiner

*Primary Examiner* — Noble E Jarrell
(74) *Attorney, Agent, or Firm* — FISHERBROYLES, LLP; Roger L. Browdy

(57) ABSTRACT

The invention relates to permethrin for use in the external treatment of *Demodex* spp. infestations, in particular in the eye area, in humans, the permethrin being used in an amount ranging from 5 mg/ml to 45 mg/ml, preferably in an amount of 7.5 mg/ml.

11 Claims, 4 Drawing Sheets

PERMETHRIN FOR USE IN THE TREATMENT OF *DEMODEX* SPECIES INFESTATION

FIELD OF THE INVENTION

The present invention relates to permethrin for use in the treatment of *Demodex* spp. infestations in humans.

BACKGROUND OF THE INVENTION

*Demodex* spp. is a type of ectoparasitic mite that lives around the hair follicles or glands on the skin of mammals. There are over 100 species, with the most common infestations in humans being *Demodex folliculorum* (human *Demodex* mites) and *Demodex brevis* (short *Demodex* mites). On healthy human skin, the number of individuals is usually low. At higher density, *Demodex* mites can cause irritation and skin diseases, usually manifested by itching, burning and redness. *Demodex* mites can also cause conditions such as rosacea, folliculitis and eyelid margin inflammation.

Treatment is usually difficult and time consuming. One of the known methods of treatment is the use of topical ivermectin (in concentrations of approx. 1%). Metronidazole (in concentrations of 0.75% or 1%) is also frequently used. Other possibilities indicated in the art are 1-2% mercury ointment, 2% metronidazole gel/ointment, 2% erythromycin ointment, 4% pilocarpine, sulfur ointment, 10% m-ethyl o-croton toluidine solution, crotamiton, camphor oil, sage oil, tea tree oil. There are also some reports of the use of permethrin on the skin in relatively high concentrations (5%) (Koçak M, Yağli S, Vahapoğlu G, Ekşioğlu M., Permethrin 5% cream versus metronidazole 0.75% gel for the treatment of papulopustular rosacea. A randomized double-blind placebo-controlled study. Dermatology, 2002, 205, 3, 265-70). Some publications indicate the effectiveness of orally applied ivermectin together with topically applied 5% permethrin (Damian D., Rogers M., *Demodex* infestation in a child with leukemia: treatment with ivermectin and permethrin. International Journal of Dermatology, September 2003, 42, 9, 724-726). In most cases, the treatment indicated is aimed at preventing skin problems. However, there are no therapies suitable also for the treatment of diseases of the eyes and eyelids associated with demodicosis, which would combine safety of use with satisfactory effectiveness.

International patent application with publication number WO19113475 and European patent EP2791354 indicate many substances that can be used as local anti-infection agents in skin diseases of various etiologies, including juvenile acne and rosacea. However, none of these documents mentions the treatment of demodicosis or *Demodex* infection. The European patent EP2310000 discusses possible treatments for rosacea, and among the potential active substances for the treatment of rosacea, among others, permethrin. This document, however, does not mention the prevention of *Demodex* spp. The European patent EP2279736 also concerns the treatment of skin diseases related to, i.a. infections such as rosacea. Treatment with casinoids is proposed and permethrin may be one of the potential additional active ingredients. International application WO20023943 relates to the use of spinosins in the treatment of eye and facial skin conditions associated with *Demodex* mites. Permethrin is also mentioned in the application, however only as an optional additional treatment supporting ingredient.

Permethrin is a synthetic organic chemical compound classified as the third generation insecticide. It belongs to the group of synthetic pyrethroids. Its structural formula is:

(I)

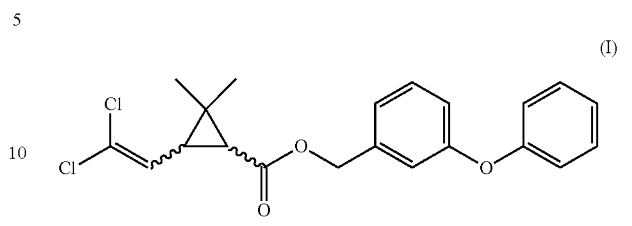

It is used in agriculture to protect crops from pests. Strongly poisonous to insects, to humans and many other higher organisms, i.a. dogs is relatively harmless (but poisonous to cats, for example). Used in veterinary medicine and health care as an ingredient in shampoos against lice, fleas and in ointments against mites, and in tropical countries as a preventive measure against insects that transmit malaria and dengue fever. As mentioned above, it has been proposed for use in the treatment of various skin conditions (although rather as an auxiliary active ingredient). Recently, it has also been suggested to use its known formulations to treat the skin, topically in the eyelid area (Hecht, Idan et al., Permethrin Cream for the Treatment of *Demodex* Blepharitis. December 2019, vol. 38/12, pp. 1513-1518), but still at a relatively high concentration of 5% (50 mg/g; 50 mg/ml), and the proposed treatment was long-term (at least 6 months). The proposed treatment was also relatively troublesome for patients, as each application required keeping the eyes closed for a long time.

Fluralaner (4-[(5R5)-5-(3,5-dichlorophenyl)-4,5-dihydro-5-(trifluoromethyl)-1,2-oxazol-3-yl]-N-[2-oxo-2-(2,2,2-trifluoroethylamino)ethyl]-o-toluamide) is an insecticide and acaricide that can be administered topically as well as orally.

Its structural formula is shown below:

(II)

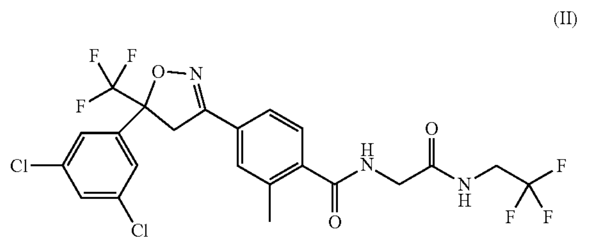

The US Food and Drug Administration (FDA) approved it under the trade name Bravecto for the treatment of fleas in dogs in May 2014. The drug blocks the normal flow of charged chloride particles (ions) into and out of nerve cells, especially those associated with gamma-aminobutyric acid (GABA) and glutamate, two substances that transfer information between nerves (neurotransmitters). It is highly selective for GABA and glutamate receptors, which block chloride channels of nerve cells, but only in arthropods. The structure of these receptors in arthropods differs from that in mammals, and only in the case of insect or arachnid receptors fluralaner fits like a key to a lock, thus being relatively safe for mammals. The use of this compound in skin demodicosis in dogs has also been described (https://www.ema.europa.eu/en/documents/overview/bravecto-epar-medicine-overview_en.pdf).

The present inventor conducted several years of research aimed at finding an effective preparation with demodicidal properties and after testing a wide group of compounds in in vitro studies, he found that both permethrin and fluralaner appear to be the most effective against difficult-to-treat conditions associated with the infestation of *Demodex* spp. such as rosacea, including in particular against eye diseases such as chronic eyelid margin inflammation and complications of the disease entity such as hordeolum, chalazions, pterygiums, dry eye syndrome. Importantly, each of these compounds turns out to be effective at relatively low concentrations and in brief contact with the parasite. So it is possible to use them in washable products, which will be more comfortable and safer for the patient.

The present invention relates to permethrin for use in the external treatment of *Demodex* spp. infestations, in particular in the vicinity of the eyes, in humans, the permethrin being used in an amount in the range 5 mg/ml to 45 mg/ml, preferably in an amount of 7.5 mg/ml.

Preferably, permethrin is used in a washable composition, in particular a shampoo and/or washing gel and/or liquid soap and/or micellar fluid.

Preferably, permethrin is applied 3 times a week, preferably regularly every 2 days.

Preferably, permethrin is used for a period of less than half a year, preferably for a period of 2 months.

Preferably, the treatment of the *Demodex* spp. infestation is directed against an ophthalmic disease or condition or symptoms, in particular against a condition selected from eyelid margin inflammation, hordeolum, chalazion, pterygium as well as dermatological symptoms in rosacea and juvenile acne.

Preferably, permethrin is used simultaneously with fluralaner.

Preferably, permethrin and fluralaner are used together in the same composition.

Preferably, permethrin and fluralaner are each used in an amount of 5 mg/ml to 30 mg/ml, preferably 5 mg/ml each.

Permethrin and/or fluralaner can be used in preparations or pharmaceutical compositions for external, topical use.

Figure 1:
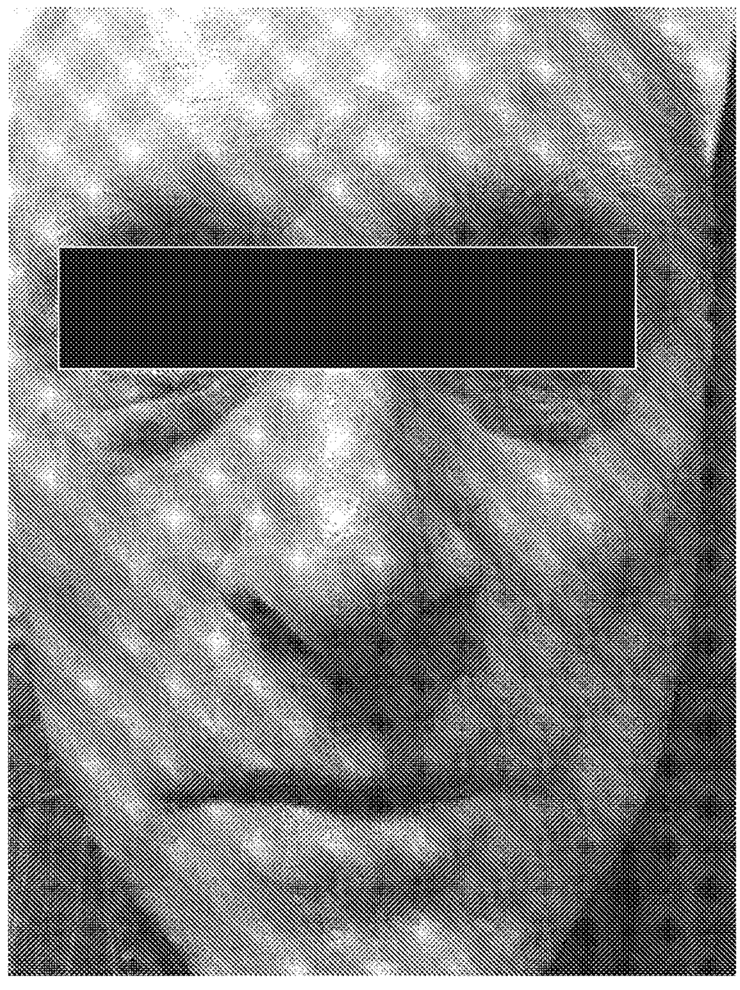
FIG. 1 shows the skin condition prior to the application of the 0.75% permethrin formulation.

The methods of formulating pharmaceutical compositions are known in the art and described in the Polish Pharmacopoeia or the European Pharmacopoeia. For example, they can be in the form of solutions or suspensions, gels, emulsions, lotions, creams, ointments, etc. Preferably, the compositions are in the form of washable preparations, such as, for example, rinse/wash solutions or suspensions for the surface of the skin or eyes or gels. The compositions can be in the form of cleansing preparations, such as shampoo, liquid soap, etc. Pharmaceutically acceptable carriers for such compositions are known in the art and may include, e.g., water, saline, oils, etc. The composition may also contain cleansing agents, e.g. surfactants. Additional and auxiliary ingredients known in the art can also be used in the composition such as thickeners, dispersants, emulsifiers, solvents, diluents, buffering agents such as acetates, citrates or phosphates, and tonicity adjusting agents such as sodium chloride or dextrose, antioxidants, preservatives, dyes and others.

Due to the possibility of a strong allergic reaction in response to the killing of a large number of *Demodex* mites and the release of antigens from their interior, both permethrin and fluralaner should be used in a much lower concentration. Each of these compounds is preferably used in an amount of 0.75%-7.5 mg/ml when used alone. They can also be used as a combined preparation containing for example 5 mg/ml permethrin (0.5%) and 5 mg/ml fluralaner (0.5%) in total.

Due to the presence of *Demodex* mites on the entire body surface, local treatment, e.g. around the eyes only (local eradication), is not effective in the long term, as after its completion, it is followed by re-colonization from other areas of the body (e.g. hairy head, chest, pubic area). Therefore, the most preferred treatment is a shampoo and gel or a liquid soap containing 0.5% (5 mg/ml) to 4.5% (45 mg/ml), preferably 0.75% (7.5 mg/ml) of permethrin or from 0.5% (5 mg/ml) to 4.5% (45 mg/ml), preferably 0.75% (7.5 mg/ml) of fluralaner or a total of 0.5% (5 mg/ml) to 3% (30 mg/ml), preferably 0.5% (5 mg/ml) of permethrin and 0.5% (5 mg/ml) to 3% (30 mg/ml), preferably 0.5% (5 mg/ml) of fluralaner. It is particularly preferred that the formulation contains 0.75% permethrin or 0.75% fluralaner or a total of 0.5% permethrin and fluralaner.

For example, treatment may be for at least 1 month or at least 2 months, and shampoo and shower gel or soap may be used for example at least 3× a week.

The treatment period according to the invention may therefore preferably be 1 month, or else 2 months, or, for example, up to 3 months, up to 4 months, up to 5 months, up to 6 months. The formulation may be used preferably 3× a week, or e.g. more frequently (e.g. 4× a week, a week, 6× a week, daily).

After each application of the above-mentioned formulations, not only the chemicals used, but also the dead individuals and antigens released from their interior are rinsed in the shower, which prevents any allergic reactions. The use of formulations in a washable form and with relatively low concentrations of the active ingredient(s) is safer and much more convenient for patients. Surprisingly, both permethrin and fluralaner appear to be effective at low concentrations and can be applied in washable formulations.

The compositions according to the invention may therefore take the form of a washable skin and/or hair care formulation, e.g. a shampoo, cleansing gel, liquid soap, micellar lotion, a rinse or rinse solution or suspension, etc.

By "washable" formulation (or in other words "rinse-off" formulation) is meant here a formulation which, when applied to the surface of the body, skin, hair or mucous membranes, or, for example, to the eye area or to the eyelids, is to be removed, for example, by rinsing it with water.

One of the advantages of the solution according to the present invention is that it allows the use of active substances in low concentrations, as well as in washable formulations, which results in a short contact of the formulation with the skin, eyes, mucous membranes, etc. Additionally, the compounds used according to the invention prove to be ticular ophthalmic diseases or conditions or symptoms, such as redness, burning, itchy eyes, dry eye with extremely effective against species of *Demodex* spp. causing skin problems, in parperiodic tearing, eyelid margin inflammation, hordeolum, chalazion, pterygium, dry eye syndrome, etc. There is no need to use additional, potent active substances such as ivermectin. There is no need for additional oral therapy or antibiotic therapy. Treatment can be shorter, less painful for the patient, and is associated with a lower risk of allergic reactions or irritation.

EXAMPLE

Example 1. Study of Acaricidal Effectiveness

Study Methodology.

289 people took part in the study; these were patients with eyelid margin inflammation, chalazion or pterygium (Table 1).

TABLE 1

Patients participating in the study

| Group No. | Group name | Total number | Female number | Male number | Average age |
|---|---|---|---|---|---|
| 1 | Patients with a chalazion | 141 | 71 | 70 | 47 |
| 2 | Patients with pterygium | 56 | 15 | 41 | 60 |
| 3 | Patients with eyelid margin inflammation | 92 | 55 | 37 | 59 |

At least ten eyelashes from the upper and lower eyelids of both eyes were randomly collected from all subjects from the subsequent groups. The collected material was assessed in a UB-203i light microscope with a five-point revolver bowl and a vision track with a magnification of 4×, 10×, 20×, 40× and 100×, archiving the results with a digital camera type Toupcam TP 601300A from Touptek Photonics installed in the device.

TABLE 2

Percentage of Demodex mites Infestation for Various Ophthalmic Conditions

| | chalazion | pterygium | chronic eyelid margin inflammation |
|---|---|---|---|
| Percentage of Demodex mites infestation | 96% | 96% | 98% |

In the case of the presence of *Demodex* mites, several dozen different chemical compounds in various concentrations with a potential demodicidal effect were used on the glass slide without the use of a coverslip. The effect of acaricidal effectiveness was observed in the UB-203i light microscope with a five-point revolver bowl and a vision track with magnification of 4×, 10×, 20×, 40× and 100×. The activity of those compounds which showed demodicosis (survival of *Demodex* mites in in vitro conditions) up to 10 minutes after administration was considered a positive result. The in vitro test results for permethrin and fluralaner were archived using a Toupcam TP 601300A digital camera from Touptek Photonics mounted on the device. The results regarding the survival time of *Demodex* mites are presented in Table 3 below.

TABLE 3

In vitro survival study of Demodex mites (on a glass slide without a coverslip) after administration of various compounds. A time has been recorded in which they no longer show signs of life (immobility and deformation of shape).

| Preparation | Concentration | Time of Survival of Demodex mites |
|---|---|---|
| Pilocarpinum hydrochloridum | 2% | more than 15 minutes |
| Tropicamidum | 1% | more than 15 minutes |
| Cyclopentolat | 1% | more than 15 minutes |
| Atropinum sulfuricum | 1% | more than 15 minutes |
| Neosynephrin (Phenylephrini hydrochloridum) | 10% | more than 15 minutes |
| Ofloxacin | 0.30% | more than 15 minutes |
| Ciprofloxacin | 0.30% | more than 15 minutes |
| Levofloxacin | 0.50% | more than 15 minutes |
| Amikacin | 0.30% | more than 15 minutes |
| Tobramycin | 0.30% | more than 15 minutes |
| Gentamicin | 0.30% | more than 15 minutes |
| Metronidazole ointment | 1.00% | more than 15 minutes |
| Metronidazole liquid | 0.50% | more than 15 minutes |
| Ivermectin | 1% | more than 15 minutes |
| Novosscabin (benzyl benzoate) | 30% | more than 15 minutes |
| Manusan (chlorhexidine digluconate) | 4% | more than 15 minutes |
| Crotamiton | 10% | more than 15 minutes |
| Ethanol | 98% | more than 15 minutes |
| Liquid parafin | 100% | more than 15 minutes |
| Hydrogen peroxide (hydrogen peroxide) | 3% | more than 15 minutes |
| Urea | 20% | more than 15 minutes |
| Tea tree oil (terpinen-4-ol) | 44% | more than 15 minutes |
| Polstigmine (neostigmine methyl sulfate) | 0.05% | more than 15 minutes |
| Permethrin | 25% | 3 minutes |
| Permethrin | 10% | 5 minutes |
| Permethrin | 0.75% | 8 minutes |
| Fluralaner | 28% | 3 minutes |
| Fluralaner | 10% | 6 minutes |
| Fluralaner | 0.75% | 9 minutes |

The highest efficiency was achieved by using a 25% solution of permethrin and a 28% solution of fluralaner (in vitro survival of *Demodex* mites up to 3 minutes). Interestingly, both of these compounds showed adequate efficacy, and even better than the compounds used and recommended in the art for use against *Demodex* mites, already at low concentrations (0.75%). For both compounds, despite such a low concentration, the loss of mobility and deformation of *Demodex* mites was observed, indicating their death, in less than 10 minutes.

Example 2. Topical Use of Permethrin

Figure 2:
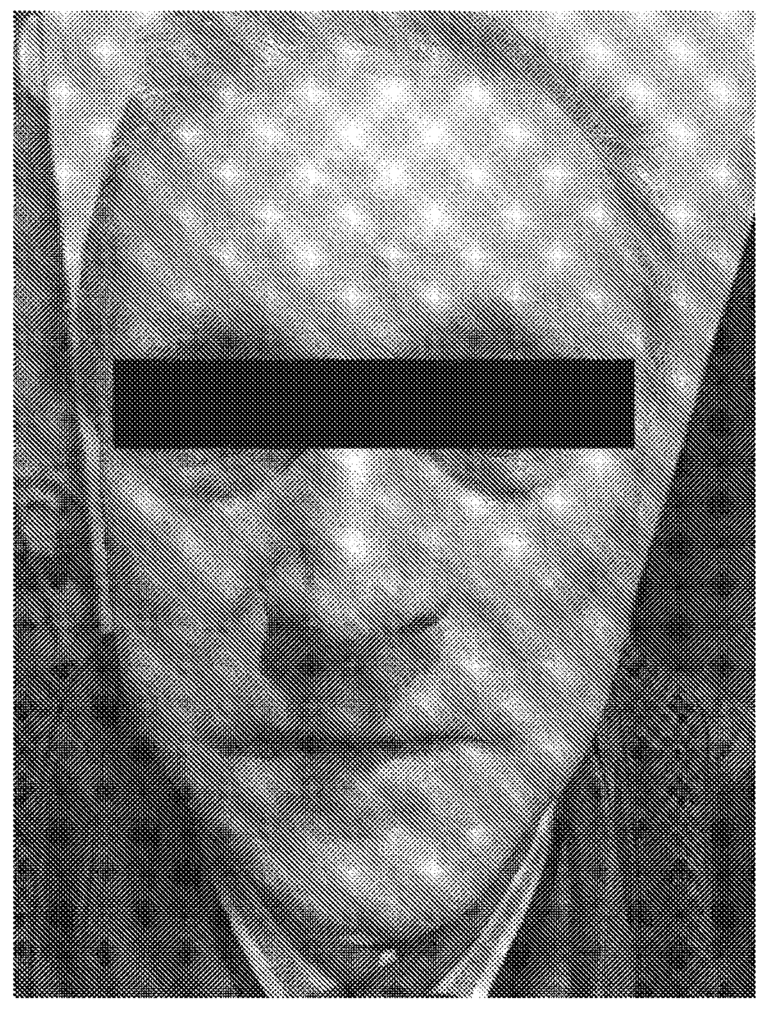
FIG. 2 shows the skin condition after application of the 0.75% permethrin formulation.

A shampoo or shower gel containing 0.75% permethrin is used 3 times a week for a period of 2 months. In a person who shows inflammation and redness (FIG. 1), there is a visible improvement after this period with a reduction in inflammation symptoms, in particular a reduction in redness (FIG. 2).

As a result of the use of the preparation, a reduction in inflammation of the eyelid margins is also observed, as well as a reduction in burning, itching in the eyes, the feeling of dry eyes, and a reduction in the appearance of scales and deposits on the edges of the eyelids.

Example 3. Use of Fluralaner in Topical Use

Figure 3:
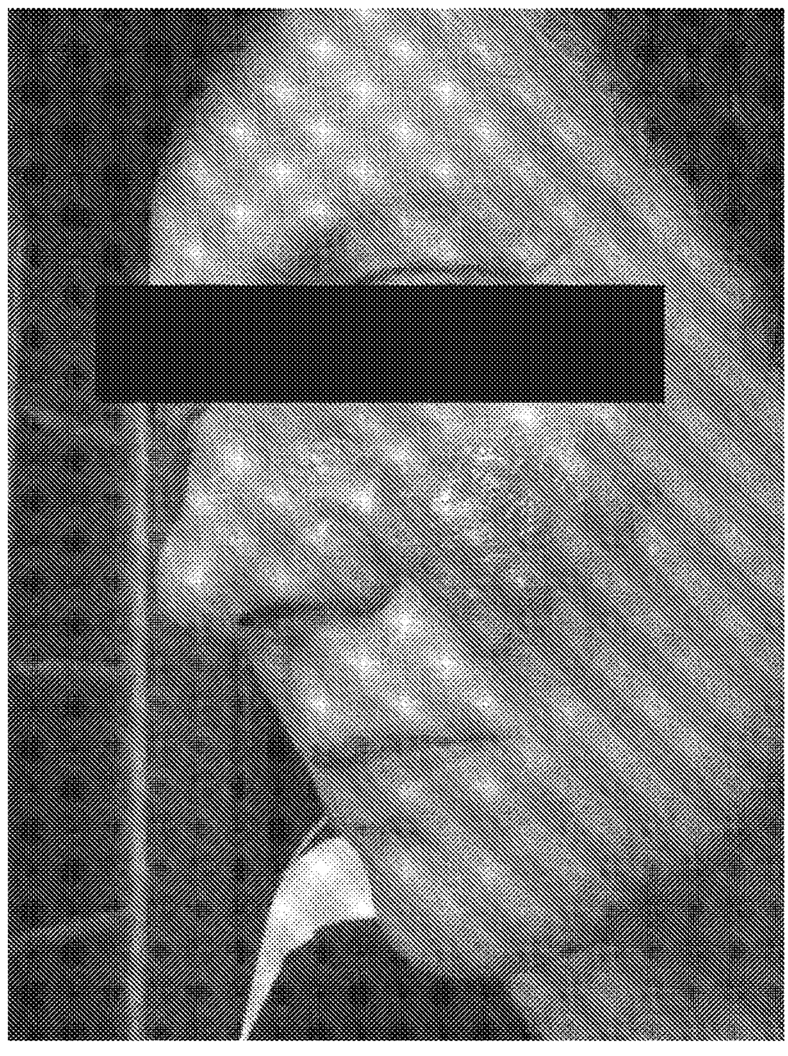
FIG. 3 shows the skin condition prior to the application of the 0.75% fluralaner formulation.
Figure 4:
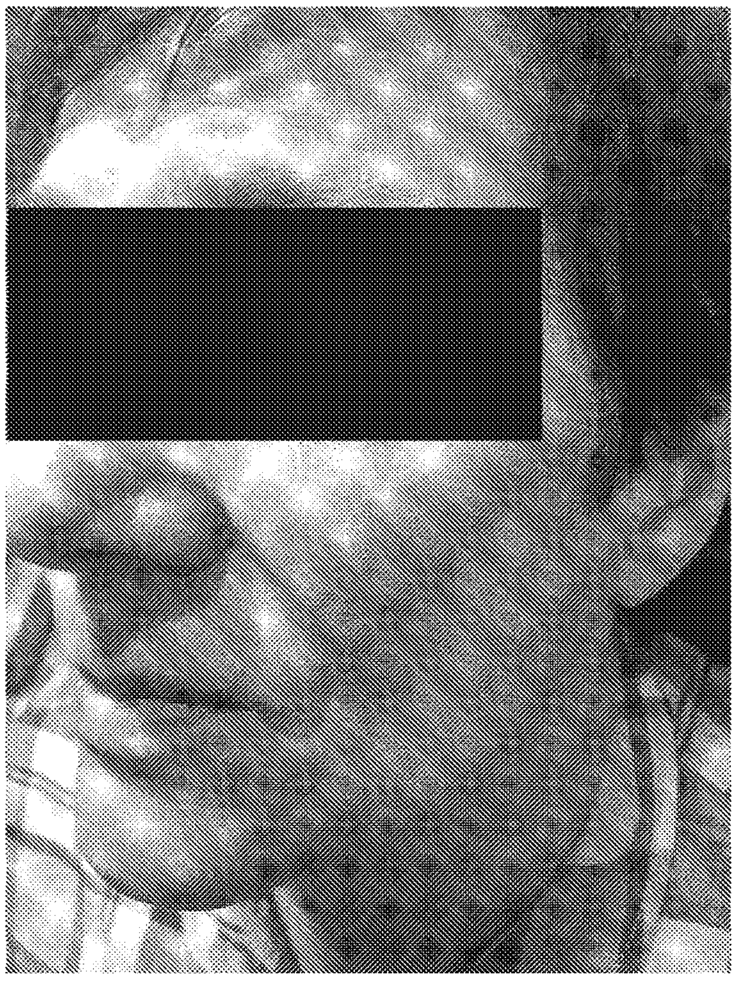
FIG. 4 shows the skin condition after application of the 0.75% fluralaner formulation.

Shampoo or shower gel containing 0.75% fluralaner is used 3 times a week for a period of 2 months. In a person who shows inflammation and redness (FIG. 3), there is a visible improvement after this period with a reduction in inflammation symptoms, in particular a reduction in redness (FIG. 4).

As a result of the use of the preparation, a reduction in inflammation of the eyelid margins is also observed, as well as a reduction in burning, itching in the eyes, the feeling of dry eyes, and a reduction in the appearance of scales and deposits on the edges of the eyelids.

Example 4. Topical Use of Permethrin and Fluralaner

A shampoo or shower gel containing 0.5% fluralaner and 0.5% permethrin is used 3 times a week for a period of 2 months. After this period, the patient shows a visible improvement with a reduction in the symptoms of inflammation of the eyelids, in particular reduction of redness and burning, itchy eyes, the feeling of dry eyes, and a reduction in the appearance of scales and deposits at the edges of the eyelids.

The invention claimed is:

1. A method for the external treatment of *Demodex* species infestations in the eye or in the eye area, in humans, comprising applying to the eye or the eye area permethrin in a water-rinseable composition in a form of shampoo and/or washing gel and/or liquid soap and/or micellar lotion or ready-made disposable wipes impregnated with said composition, wherein a concentration of permethrin ranges from 5 mg/ml to 45-30 mg/ml.

2. A method for the external treatment of *Demodex* species infestations in the eye or in the eye area, in humans, comprising applying to the eye or the eye area permethrin in a water-rinseable composition in a form of shampoo and/or washing gel and/or liquid soap and/or micellar lotion or ready-made disposable wipes impregnated with said composition, wherein a concentration of permethrin ranges from 5 mg/ml to 30 mg/ml, wherein said permethrin is applied 3 times a week, for a period of less than half a year.

3. The method according to claim 2, wherein said permethrin is applied for a period of 2 months.

4. A method for the external treatment of *Demodex* species infestations in the eye or in the eye area, in humans, comprising applying to the eye or the eye area permethrin in a water-rinseable composition in a form of shampoo and/or washing gel and/or liquid soap and/or micellar lotion or ready-made disposable wipes impregnated with said composition, wherein a concentration of permethrin ranges from 5 mg/ml to 45 mg/ml, said treatment of the *Demodex* species infestation is being directed against an ophthalmic disease or condition or symptoms, wherein said ophthalmic disease or condition is selected from eyelid margin inflammation, hordeolum, chalazion, and pterygium.

5. A method for the external treatment of *Demodex* species infestations in the eye or in the eye area, in humans, comprising applying to the eye or the eye area permethrin in a water-rinseable composition in a form of shampoo and/or washing gel and/or liquid soap and/or micellar lotion or ready-made disposable wipes impregnated with said composition, wherein a concentration of permethrin ranges from 5 mg/ml to 45 mg/ml, the method further comprising applying fluralaner simultaneously with said permethrin.

6. The method according to claim 5, wherein said composition includes both permethrin and fluralaner.

7. The method according to claim 5, wherein said permethrin and said fluralaner are each used in an amount ranging from 5 mg/ml to 30 mg/ml.

8. The method according to claim 4, wherein said composition is retained in the eye area for less than 10 minutes.

9. The method according to claim 1, wherein said concentration of permethrin is in an amount of 7.5 mg/ml.

10. The method according to claim 2, wherein the composition is applied regularly every 2 days.

11. The method according to claim 7, wherein said permethrin and said fluralaner are each used in an amount of 5 mg/ml.

* * * * *